United States Patent [19]

Rice

[11] 3,985,015
[45] Oct. 12, 1976

[54] IMPACT WEAR TESTING DEVICE

[76] Inventor: Stephen L. Rice, 9 Storrs Heights Road, Storrs, Conn. 06268

[22] Filed: Nov. 20, 1975

[21] Appl. No.: 633,851

[52] U.S. Cl. ................................................. 73/12
[51] Int. Cl.² ........................................... G01N 3/34
[58] Field of Search ........................ 73/12, 79, 7, 82

[56] References Cited
UNITED STATES PATENTS

| | | | |
|---|---|---|---|
| 3,498,117 | 3/1970 | Dalrymple | 73/79 |
| 3,788,466 | 1/1974 | Wilson | 73/12 X |
| 3,879,982 | 4/1975 | Schmidt | 73/82 X |

Primary Examiner—Charles A. Ruehl

[57] ABSTRACT

An impact wear testing device comprises a driven member mounted for controlled oscillations along an axis and a rotatably mounted support member having an impact portion aligned with the driven member axis. The driven member oscillates so that one end thereof periodically contacts the support member impact portion. The wear testing device has means for mounting a specimen to be tested on either the end of the driven member or support member impact portion and a force measuring device disposed on the other of these two elements. Control means may be provided to monitor the output of the force measuring device and to vary the driven member oscillations to maintain the peak impact force at a constant value. The force measuring device is preferably a time responsive piezoelectric transducer, and may have means for mounting a test specimen thereto to provide two body impact wear testing.

21 Claims, 3 Drawing Figures

IMPACT WEAR TESTING DEVICE

BACKGROUND OF THE INVENTION

Devices designed to measure the amount of wear a specimen undergoes under certain conditions are well known. A common device applied a measurable load upon a test specimen which is a common contact with a companion surface and undergoes sliding motion relative thereto. The size of the wear scar is measured as a function of the load, relative sliding speed, and number of oscillations.

More recently, the study of the wear process occuring under conditions of impact loading has proven to be of significance, as mechanical components which make repeated contact under impulsive loads are typical of virtually all hardware designed for dynamic operation. In an increasing number of situations, such components operate without benefit of an external lubricant since solid lubricants, and self-lubricating or wear-resistant materials have been developed for such applications. In some cases the sliding wear resistance of these materials have been evaluated, but there has been little laboratory investigation of impact loading wear.

Several devices have been developed for studying impact wear, one being that of R. G. Bayer et al and described in 19 Wear pp. 343–354 (1972). This device fires test projectiles against a flywheel, normal impact occuring when the flywheel is stationary and sliding impact having force components normal and tangential to the flywheel occurring when it is rotating. The wear of the projectiles is measured by a profilometer after a given number of impacts. Since the projectile is unconstrained, it may be accelerated to varying degrees transverse to its direction of incidence during impact, so that there results a variable relative sliding velocity. This renders anaylsis of test data difficult. Furthermore, the device of Bayer et al provides no means for measuring the impact force pulse.

Another wear testing device is that of E. A. Pamfilov of the Soviet Union and described in 37 *Zavodskaya Laboratoriya* No. 5, pp. 620–621 (1971). His machine, by cams and springs, permits either impact or constant loading on a test specimen. No provision is made for measuring the impact impulse.

Other wear testing devices are deficient in that they do not provide for measurement of critical parameters such as impact force as a function of time and thus loading impulses, or permit combined normal incidence/sliding impact wear studies wherein the sliding contact is constant throughout the impact. They are also deficient in that it is quite difficult to maintain a constant impact force over a series of impacts as a test specimen undergoes wear.

Accordingly, it is an object of the present invention to provide a novel impact wear testing device capable of providing repetitive impacts to test specimens under either normal or sliding impact and in which the impact is easily measurable and reproducible.

It is also an object to provide such an impact wear testing device capable of maintaining the peak impact force at a desired magnitude.

Another object is to provide such a device providing convenient adjustability of the normal and tangential components of the load impulses applied to a test specimen and a constant relative sliding velocity between impacting materials during sliding impact.

A further object is to provide such a device providing a simple and direct measure of the impact force as a function of time.

SUMMARY OF THE INVENTION

It has now been found that the foregoing and related objects of the present invention may be readily attained in an impact wear testing device comprising drive means, a base, and a driven member mounted on the base for reciprocating movement along a first axis and operatively connected to the drive means for controlled oscillations along the first axis. A support member is rotatably mounted on the base for rotation and has an impact portion aligned with the first axis, the support member being operatively connected to drive means for rotation thereof and the driven member being oscillatable to bring one end adjacent the support member impact portion. One of a pair of impact wear testing elements comprising specimen mounting means and force measuring means is disposed upon the aforementioned end of the driven member and the other of the testing elements is disposed upon the support member impact portion whereby a specimen mounted on the specimen mounting means impacts periodically with the force measuring means during oscillation of the driven member. Control means responsive to the force measuring means is operable upon the drive to vary the oscillations of the driven member.

The support member is preferably rotatble about a second axis parallel to the first axis and the specimen mounting means is disposed upon the driven member with the force measuring means being disposed upon the support member impact portion.

The force measuring means is operable to convert an impact force thereon to a time dependent output voltage proportional thereto, the control means comparing the peak output voltage to a reference voltage corresponding to a desired maximum impact force and altering the oscillation of the driven member in response to deviation of the output voltage from the reference voltage whereby the impact force is maintained generally constant at the desired value. Readout means may be connected in circuit relation with the force measuring means operable to indicate the force exerted thereon.

The drive means preferably comprises a rotatable member mounted on the base for rotation and pivotable upon the base to vary the angular orientation of the axis of rotation of the rotatable member relative to the first axis. A connecting rod has one end eccentrically mounted on the rotatable member and the other end connected to the other end of the driven member whereby altering the angular orientation of the rotational axis of said rotatable member will vary the movement of the driven member toward the support member.

The control means may be omitted from the impact wear testing device, or the support member may be stationary to provide normal impact between a test specimen and the force measuring means.

DETAILED DESCRIPTION OF THE ILLUSTRATED EMBODIMENT

Figure 1:
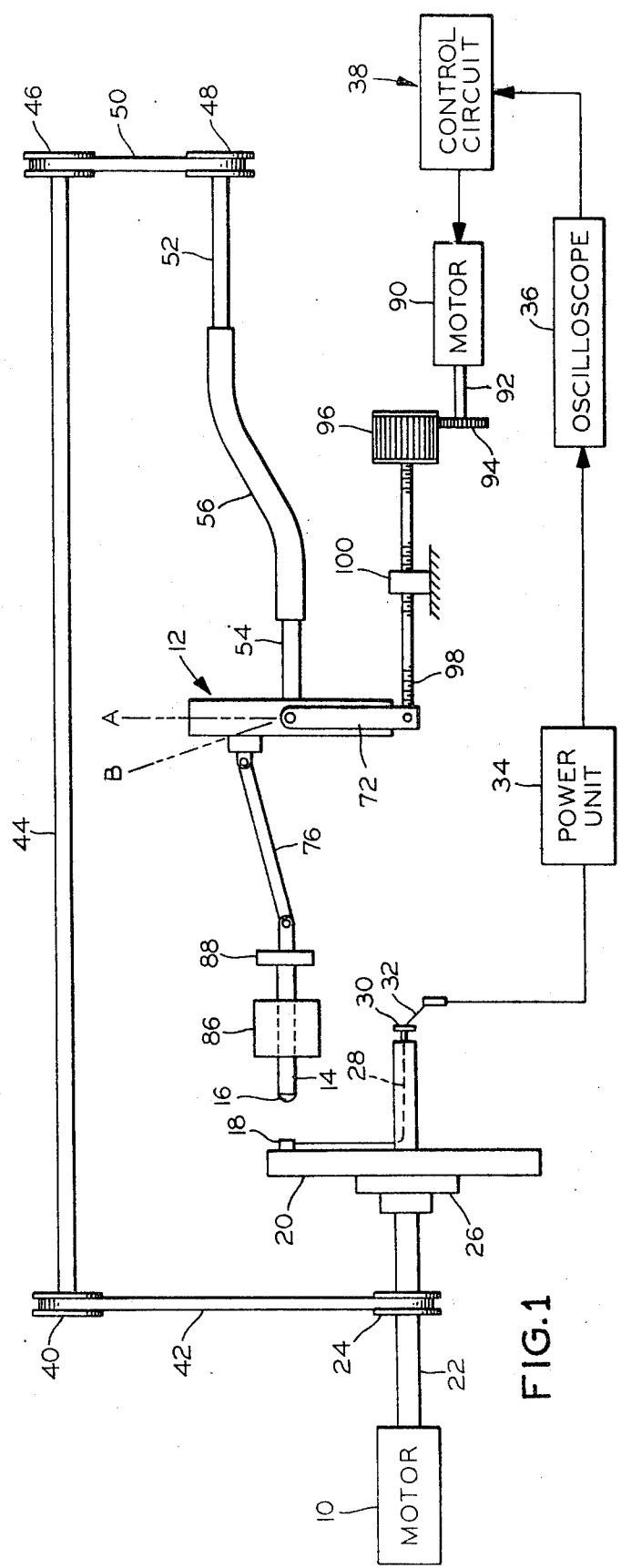
FIG. 1 is a diagrammatic illustration of an impact wear testing machine embodying the present invention.

Turning now to the attached drawings in detail, illustrated diagrammatically in FIG. 1 thereof is an impact wear testing device embodying the present invention which comprises drive means including a motor 10, a variable amplitude oscillator generally designated by the numeral 12, and a driven member 14 operatively connected to the oscillator 12 for longitudinal oscillations thereof. A test specimen 16 is mounted upon the free end of the driven member 14 for periodic impact upon a force measuring device 18 which is mounted upon a portion of the rotatable support member 20 which rotates into alignment with the axis of the driven member 14.

The motor 10 is of conventional design and has a shaft 22 rotatable at variable controlled speeds. Mounted on the shaft 22 for rotation therewith are a pulley 24 and the support member 20, and a disengageable coupling 26 links the two portions of the shaft 22. Two modes of operation will be described hereinafter, one of which requires that the support member 20 be stationary with the force measuring device 18 in alignment with the driven member axis while the other requires that the support member 20 rotate. The coupling 26 functions in a known manner to permit both modes of operation, external means (not shown) such as a clamp or brake being provided to prevent any rotation of the support member 20 when the non-rotating mode is desired.

The force measuring device 18 or transducer is secured to a face of the suppoort member 20 at a point spaced from its axis of rotation and is operable to convert an impact force thereon to a time dependent output voltage proportional thereto. The force measuring device 18 is connected by a coaxial cable 28 to a slip disc 30 on the end of the shaft 22. The disc 30 in turn contacts the contact brush 32 which is connected to a power unit 34 used in conjunction with the force measuring device 18 and providing power thereto. An oscilloscope 36 receives and displays the output signal of the force measuring device 18, and the signal is also fed through the power unit 34 and oscilloscope 36 into a control circuit generally designated by the numeral 38 for a purpose to be described hereinafter.

The pulley 24 is operatively connected by the belt 42 to a pulley 40 mounted on a shaft 44 which is supported in a conventional manner for low friction rotation. Also secured to the shaft 44 for rotation therewith is a pulley 46, which is operatively connected by a belt 50 to a pulley 48 on a shaft 52. The flexible connector 56 operatively connects the shaft 52 to the shaft 54 which in turn is secured to the variable amplitude oscillator 12 to impart rotation thereto. Pulleys 24, 40, 46, 48 have the same diameter so that the shaft 22 and oscillator 12 have the same frequency of rotation.

Figure 3:
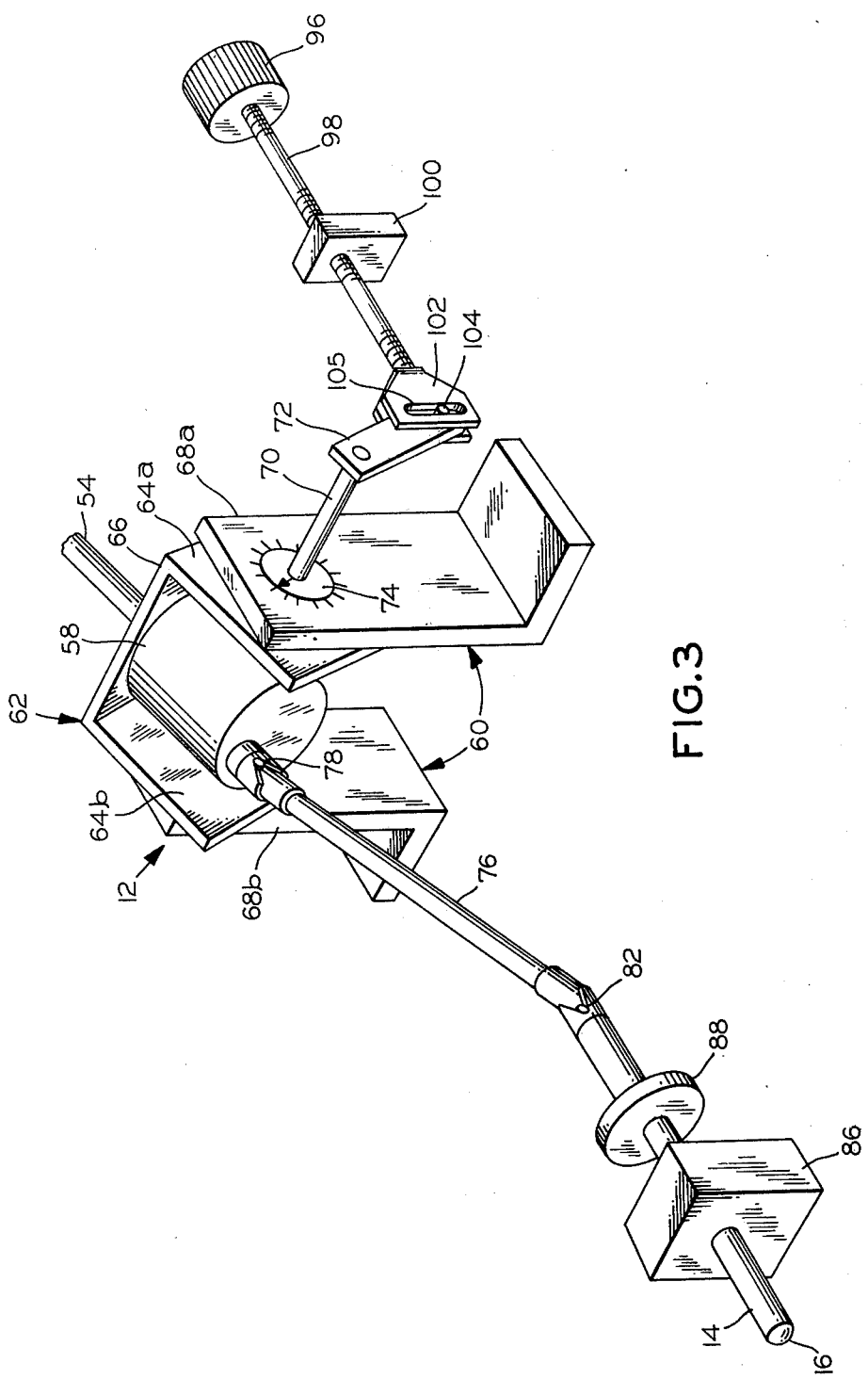
FIG. 3 is a perspective view of a driven member and a portion of a drive means and control means.

With reference to FIG. 3, the variable amplitude oscillator 12 includes a rotatable member 58, a pair of L-shaped support members generally designated by the numeral 60, and a controllably pivotable U-shaped mount generally designated by the numeral 62 for rotatably supporting the rotatable member 58 and which is itself pivotably supported upon the support members 60 for pivoting about an axis perpendicular to the axis of rotation of the rotatable member therein.

More particularly, the rotatable member is supported between the legs 64a, 64b of the mount 62 upon the shaft 54 which is supported in a bearing (not shown) within the web 66 of the mount 62. The mount 62 is supported between the upright legs 63a, 68b of the base members 60 for pivotal movement about an axis perpendicular to the rotor axis of rotation upon stub shafts 70, one of which has an arm 72 depending from the end thereof to effect controlled pivoting of the mount 62 and rotatable member 58 within the support members 60. A dial and indicator 74 facilitates reproducibility of the angular orientation of the axis of rotation of the rotatable member 58.

Pivotably connected to the outer face of the rotatable member 58 by the universal joint 78 is one end of the connecting rod 76 which is connected at its other end to the driven member 14 by the universal joint 82. Pivotal and rotational movement occur at both connections as the connecting rod 76 rotates about the axis of rotation of the rotatable member 58. The driven member 14 is slidably seated in a bearing block 86 and has a key (not shown) engaging a slot (not shown) in the block 86 to prevent rotation of the portion of the member 14 constrained therein. A bearing member 88 is mounted to the member 14 and functions in a known manner to decouple rotation of the portion of member 14 intermediate member 88 and joint 82 from that constrained within block 86.

The amplitude of driven member oscillations and thus impact force is maintained generally constant at a predetermined level by the control circuit 38 and d.c. motor 90. The circuit 38 functions in a manner described hereinafter to compare the maximum output voltage V of the force measuring device 18 to a reference voltage Vo corresponding to a desired peak impact force and has an output voltage corresponding to the difference between V and Vo. This output voltage, if any, from the circuit 38 drives the motor 90 which has mounted upon its shaft 92 a gear 94 which engages a gear 96 mounted on a shaft 98 which is threadably seated for axial movement in the block 100.

Rotatably secured to the other end of the shaft 98 is a U-shaped bracket 102 which straddles and is pivotably secured to the arm 72 by a pin 104 which slidably seats in slots 105 in the legs of the bracket 102. The pin 104 extends through an aperture (not shown) in the arm 72. Thus, as the shaft 92 and gear 94 rotate, they affect rotation of the gear 96 and shaft 98 which moves axially in the block 100 as it rotates by reason of its threaded engagement therein. This axial movement effects pivoting of the arm 72 and thereby the mount 62 and rotatable member 58 about an axis through the stub shafts 70.

Figure 2:
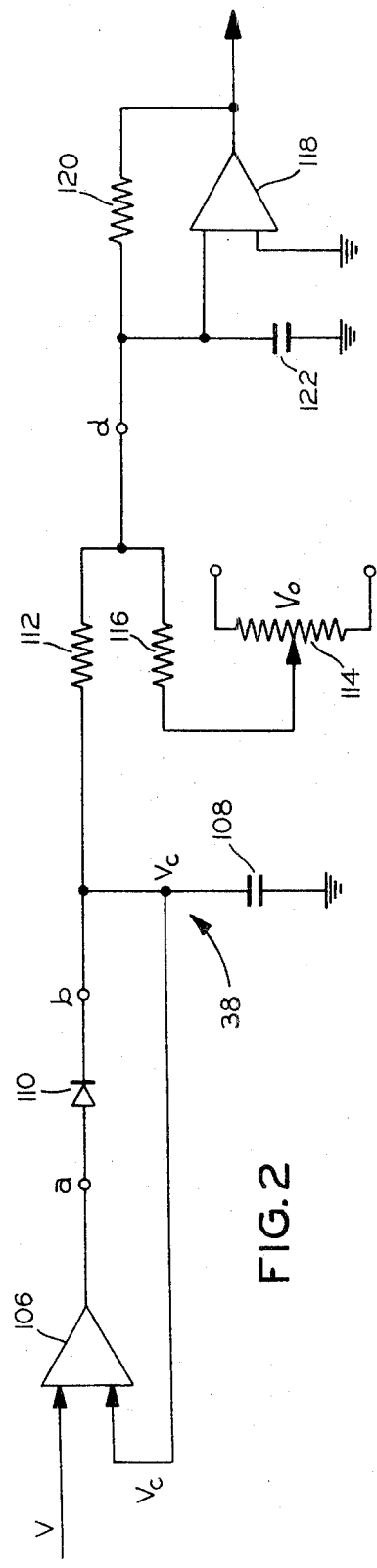
FIG. 2 is a diagrammatic illustration of a control circuit.

The control circuit 38 shown in FIG. 2 functions generally to "capture" the maximum output voltage of the force measuring device 18 in a capacitor 108, then compares this maximum voltage to a reference voltage corresponding to a desired impact force, and passes any difference voltage to the motor 90. As previously described, the motor 90 when energized effects control of the angular orientation of the rotational axis of the rotatable member 58.

The pulsed output voltage V of the force measuring device 18, which has passed through the power unit 34 and oscilloscope 36, is fed into an operational amplifier 106. the output of the amplifier 106 is the amplified difference between V and the voltage on the capacitor 108. Vc, which is fed back into the amplifier 106. The signal from the amplifier 106 passes to a diode 110 which is conducting as long as the voltage at point a, Va, exceeds that at point b, Vb. As V increases toward its maximum value, Vc will also be increasing as the amplified Va exceeds Vb. When V reaches its maximum value, the capacitor 108 is fully charged to the maximum value of V, and at that point V is equal to Vc and Va is zero. The diode 110 will be non-conducting until V exceeds Vc during the succeeding pulse at which time Va will be greater than Vb. The maximum value of V is thus "captured" in the capacitor 108.

The capacitor 108 will discharge with a time constant equal to the product of the capacitance of capacitor 108 and resistance of resistor 112. Because of this discharge, which is designed to be relatively slow, the reference voltage Vo to which Vc is compared is initially set to the average value of Vc during the impact in which the desired impact force is determined.

The reference voltage Vo is set at negative Vo on a potentiometer 114, its external power source being omitted from the schematic illustration. Resistors 112, 116 have the same resistance and thus the voltage at point d, Vd, is equal to the difference between the instantaneous Vc (corresponding to the maximum V) and Vo. The voltage Vd, which corresponds to the deviation of the actual peak impact force from the desired peak force, is fed into an operational amplifier 118, a resistor 120 and capacitor 122 operating as a low pass filter to smooth transients in the system and allow only sustained error messages to get through. The output of amplifier 118 is then power amplified as required (amplifier not shown) to provide the input signal to motor 90, which then rotates gear 94, the direction of rotation depending on the sign of the input signal and the amount of rotation depending on the magnitude of the input signal. Rotation of the gear 94 effects adjustment of the angular orientation of the rotational axis of the rotatable member 58 in a manner described hereinbefore.

The manner of operation and function of the impact wear testing device will now be described, the mode providing for normal impact between the specimen 16 and force measuring device 18 being discussed first. In this mode the two portions of the shaft 22 are uncoupled and the support member 20 secured so that the force measuring device 18 is aligned with the axis of the driven member 14. The motor 10 effects rotation of the rotatable member 58 in a manner described hereinbefore.

When the rotatable member 58 of the oscillator 12 is in the position indicated by the dashed line A in FIG. 1, no oscillations of the driven member 14 will occur. Upon pivoting the rotatable member 58 to the position indicated by the dashed line B (see also FIG. 3), the driven member 14 will oscillate longitudinally at the same frequency at which the rotatable member 58 rotates. The angle between lines A and B determines the amplitude of driven member oscillations and thus the impact force, while the rotational frequency of the shaft 22 determines the frequency of oscillations of the driven member.

Sliding impact collisions having both a normal and tangential force component relative to the impacting elements are provided by coupling the two portions of the shaft 22 through the coupling 26. Since the shaft 22 and support member 20 rotate at the same frequency as the driven member 14 oscillates, an impact between the specimen 16 and force measuring device 18 occurs once per rotation of the shaft 22.

The driven member 14 is constrained by the block 86 to move axially, thus providing a constant relative sliding velocity between the specimen 16 and force measuring device 18 during impact. This constraint effectively eliminates any transverse acceleration of the specimen 16 during impact, which would render data analysis extremely complicated. Varying the frequency of rotation of the shaft 22 varies the relative sliding velocity of the impacting elements as well as the frequency of impacts as with the normal impact mode, the amplitude of slider oscillations controls the impact force.

As the specimen 16 wears during a series of impacts, the impact force will decrease somewhat if the amplitude of driven member oscillations remains constant. To counteract this effect and maintain the peak impact force generally constant, the control circuit 38 and motor 90 function in a manner described hereinbefore to effect compensating pivotal movement of the rotatable member 58 about its pivotal axis.

The amount of wear a test specimen has undergone is physically measured using a profilometer, this data being obtained as a function of the number of impacts, impact force, relative sliding speed if any, and surface characteristics of the specimen. Qualitative analysis of the wear process may be obtained by using scanning electron microscopy techniques.

The support member 20 is rotatable at rates varying between 0 rpm (normal impact) and about 1700 rpm. At 1700 rpm the relative sliding velocity between impacting elements is about 700 inches/second, depending upon the spacing between the shaft 22 and force measuring device 18. The maximum amplitude of driven member oscillations is on the order of ½ inch.

The surface of the force measuring device impacting with the test specimen is normally hardened steel to provide testing of the specimen wear characteristics relative to steel. For wear studes involving material combinations which do not include hardened steel as one of the wear constituents, a thin coating of the subject material may be applied to the force measuring device surface. No significant attenuation of the impact force will result if the thickness of the coating is on the order of 0.005 inch or less.

The force measuring device is preferably a piezoelectric transducer having a fast response (on the order of 10 microseconds), high load carrying ability (up to 10,000 pounds), a high level output (on the order of 10 volts), and low impedance (on the order of 100 ohms). Electronic amplification of the signal is accomplished within the transducer, thus allowing the low impedance output which may be transmitted efficiently through the coaxial cable. Exemplary of such transducers are those sold by PCB Piezotronics, Inc. of Buffalo, N.Y.

The power unit is designed to operate in conjunction with the above described transducer, accepting line power and providing constant current excitation to the transducer. It also permits static (non-impact) load calibration of the transducer, and has a connection so that the transducer output may be displayed on any convenient readout device. This type of power unit is also available through PCB Peizotronics, Inc.

The preferred manner for changing the amplitude of driven member oscillations to maintain the impact force constant has been described. Alternately, the control circuit may be disconnected and the orientation of the rotatable member axis changed manually. The position of the driven member may be changed with or without altering the amplitude of oscillations to effect a change in impact force by providing for physical relocation of its drive assembly. There may be applications when it is not necessary to maintain the impact force constant; in this case the control circuit may be disconnected.

In the preferred aspect the axis of driven member oscillations is parallel to the support member axis of rotation with the force measuring device eccentrically mounted to a face thereof. Alternately, the force measuring device may be mounted on the circumferential edge of the support member with the two axes perpendicular. The two axes may be skew to provide yet another mode of impact wear study.

Thus, it can be seen the present invention provides a novel impact wear testing device which is capable of providing repetitive impacts to test specimens under either normal or sliding impact wherein the impacts are easily measurable and reproducible. The device has the capability of maintaining the peak impact force at a desired value and provides a simple and direct measure of the impact force as a function of time. The normal and tangential components of the load impulses applied to a test specimen are conveniently adjustable and there is a constant relative sliding velocity between impacting materials during sliding impact.

Having thus described the invention, I claim:

1. In an impact wear testing device, the combination comprising
   a. drive means;
   b. a base;
   c. a driven member mounted on said base for reciprocating movement along a first axis and operatively connected to said drive means for controlled oscillations along said first axis;
   d. a support member rotatably mounted on said base for rotation and having an impact portion aligned with said first axis, said support member being operatively connected to said drive means for rotation thereof, said driven member being oscillatable to bring one end adjacent said support member impact portion;
   e. a pair of impact wear testing elements comprising specimen mounting means and force measuring means, one of said testing elements being disposed upon said one end of said driven member and the other of said testing elements being disposed upon said support member impact portion whereby a specimen mounted on said specimen mounting means impacts periodically with said force measuring means during oscillation of said driven member; and
   f. control means responsive to said force measuring means operable upon said drive means to vary the oscillations of said driven member.

2. The impact wear testing device of claim 1 further including second specimen mounting means disposed upon said force measuring means.

3. The impact wear testing device of claim 1 wherein said support member is rotatable about a second axis parallel to said first axis.

4. The impact wear testing device of claim 1 wherein said specimen mounting means is disposed upon said driven member and said force measuring means is disposed upon said support member impact portion.

5. The impact wear testing device of claim 1 wherein said force measuring means is operable to convert an impact force thereon to an output voltage proportional thereto, said control means comparing the peak output voltage to a reference voltage corresponding to a desired impact force and altering the oscillations of said driven member in response to deviation of said output voltage from said reference voltage whereby the impact force is maintained generally constant at the desired value.

6. The impact wear testing device of claim 5 wherein said force measuring device output voltage is time dependent.

7. The impact wear testing device of claim 1 further including readout means connected in circuit relation with said force measuring means operable to indicate the force exerted thereon.

8. The impact wear testing device of claim 1 wherein said drive means comprises a rotatable member mounted on said base for rotation and pivotable upon said base to vary the angular orientation of the axis of rotation of said rotatable member relative to said first axis and a connecting rod having one end eccentrically mounted on said rotatable member and the other end connected to the other end of said driven member whereby altering the angular orientation of said rotational axis of said rotatable member will vary the movement of said one end of said driven member toward said support member.

9. In an impact wear testing device, the combination comprising:
   a. drive means;
   b. a base;
   c. a driven member mounted on said base for reciprocating movement along a first axis and operatively connected to said drive means for controlled oscillations along said first axis;
   e. a support member mounted on said base and having an impact portion aligned with said first axis, said driven member being oscillatable to bring one end adjacent said support member impact portion;
   e. a pair of impact wear testing elements comprising specimen mounting means and force measuring means, one of said testing elements being disposed upon said one end of said driven member and the other of said testing elements being disposed upon said support member impact portion whereby a specimen mounted on said specimen mounting means impacts periodically with said force measuring means during oscillation of said driven member; and
   f. control means responsive to said force measuring means operable upon said drive means to vary the oscillations of said driven member.

10. The impact wear testing device of claim 9 further including second specimen mounting means disposed upon said force measuring means.

11. The impact wear testing device of claim 9 wherein said specimen mounting means is disposed upon said driven member and said force measuring means is disposed upon said support member impact portion.

12. The impact wear testing device of claim 9 wherein said force measuring means is operable to convert an impact force thereon to an output voltage porportional thereto, said control means comparing the peak output voltage to a reference voltage corresponding to a desired impact force and altering the oscillations of said driven member in response to deviation of said voltage from said reference voltage whereby the impact force is maintained generally constant at the desired value.

13. The impact wear testing device of claim 12 wherein said force measuring device output voltage is time dependent.

14. The impact wear testing device of claim 9 further including readout means connected in circuit relation with said force measuring means operable to indicate the force exerted thereon.

15. The impact wear testing device of claim 9 wherein said drive means comprises a rotatable member mounted on said base for rotation and pivotable upon said base to vary the angular orientation of the axis of rotation of said rotatable member relative to said first axis and a connecting rod having one end eccentrically mounted on said rotatable member and the other end connected to the other end of said driven member whereby altering the angular orientation of said rotational axis of said rotatable member will vary the movement of said one end of said driven member toward said support member.

16. In an impact wear testing device, the combination comprising
   a. drive means;
   b. a base;
   c. a driven member mounted on said base for reciprocating movement along a first axis and operatively connected to said drive means for controlled oscillations along said first axis;
   d. a support member rotatably mounted on said base for rotation and having an impact portion aligned with said first axis, said support member being operatively connected to said drive means for rotation thereof, said driven member being oscillatable to bring one end adjacent said support member impact portion;
   e. a pair of impact wear testing elements comprising specimen mounting means and force measuring means, one of said testing elements being disposed upon said one end of said driven member and the other of said testing elements being disposed upon said support member impact portion whereby a specimen mounted on said specimen mounting means impacts periodically with said force measuring means during oscillation of said driven member.

17. The impact wear testing device of claim 16 further including second specimen mounting means disposed upon said force measuring means.

18. The impact wear testing device of claim 16 wherein said support member is rotatable about a second axis parallel to said first axis.

19. The impact wear testing device of claim 16 wherein said specimen mounting means is disposed upon said driven member and said force measuring means is disposed upon said support member impact portion.

20. The impact wear testing device of claim 16 further including readout means connected in circuit relation with said force measuring means operable to indicate the force exerted thereon.

21. The impact wear testing device of claim 16 wherein said drive means comprises a rotatable member mounted on said base for rotation and pivotable upon said base to vary the angular orientation of the axis of rotation of said rotatble member relative to said first axis and a connecting rod having one end eccentrically mounted on said rotatable member and the other end connected to the other end of said driven member whereby altering the angular orientation of said rotatable member will vary the movement of said one end of said driven member toward said support member.

* * * * *

UNITED STATES PATENT AND TRADEMARK OFFICE
CERTIFICATE OF CORRECTION

PATENT NO. : 3,985,015
DATED : October 12, 1976
INVENTOR(S) : Stephen L. Rice

It is certified that error appears in the above-identified patent and that said Letters Patent are hereby corrected as shown below:

Column 8, line 67, before "voltage" (first occurrence) insert

-- output --.

Signed and Sealed this

Twenty-second Day of February 1977

[SEAL]

Attest:

RUTH C. MASON
*Attesting Officer*

C. MARSHALL DANN
*Commissioner of Patents and Trademarks*